(12) United States Patent
Lin et al.

(10) Patent No.: US 11,746,125 B2
(45) Date of Patent: Sep. 5, 2023

(54) BIOMIMETIC PEPTIDES DERIVED FROM BIOLOGICAL SOURCE AND THEIR USES IN RETARDING AGING AND IMPROVING SKIN

(71) Applicant: TCI CO., LTD., Taipei (TW)

(72) Inventors: Yung-Hsiang Lin, Taipei (TW); Yu-Ling Wang, Taipei (TW)

(73) Assignee: TCI CO., LTD., Taipei (TW)

( * ) Notice: Subject to any disclaimer, the term of this patent is extended or adjusted under 35 U.S.C. 154(b) by 0 days.

(21) Appl. No.: 17/475,006

(22) Filed: Sep. 14, 2021

(65) Prior Publication Data

US 2021/0395304 A1 Dec. 23, 2021

Related U.S. Application Data

(62) Division of application No. 16/702,385, filed on Dec. 3, 2019, now Pat. No. 11,155,579.

(60) Provisional application No. 62/871,216, filed on Jul. 8, 2019, provisional application No. 62/871,260, filed on Jul. 8, 2019.

(51) Int. Cl.
*C07K 7/06* (2006.01)
*A61K 8/64* (2006.01)
*A61Q 19/00* (2006.01)
*A61Q 19/08* (2006.01)
*A61K 38/00* (2006.01)

(52) U.S. Cl.
CPC ............. *C07K 7/06* (2013.01); *A61K 8/64* (2013.01); *A61Q 19/007* (2013.01); *A61Q 19/08* (2013.01); *A61K 38/00* (2013.01)

(58) Field of Classification Search
CPC ........ C07K 7/06; A61Q 19/007; A61Q 19/08; A61K 8/64; A61K 38/00
See application file for complete search history.

(56) References Cited

U.S. PATENT DOCUMENTS

| | | |
|---|---|---|
| 2007/0055049 A1 | 3/2007 | Howard et al. |
| 2018/0360720 A1 | 12/2018 | Huang et al. |
| 2019/0040100 A1 | 2/2019 | Chung et al. |
| 2019/0153030 A1 | 5/2019 | Peschard et al. |

FOREIGN PATENT DOCUMENTS

| | | |
|---|---|---|
| JP | 2000060562 A | 2/2000 |
| KR | 20180019960 A | 2/2018 |
| WO | Wo-0131019 A2 | 5/2001 |
| WO | WO-2010037395 A2 | 4/2010 |
| WO | WO-2016172722 A1 | 10/2016 |
| WO | WO-2017189963 A1 | 11/2017 |

OTHER PUBLICATIONS

Fry et al (J. Mol. Evol., 2009, 68(4), 311-321). (Year: 2009).*
Legge et al, Aust.J.Biol.Sci., 1964, 17, 561-71 (Year: 1964).*
Deterding et al, 1991, 554, 73-82 (Year: 1991).*
Partial Search Report corresponding European Patent Application No. 19203345.4, dated Apr. 22, 2020 for the; (pp. 13).
Extended Search Report corresponding European Patent Application No. 19203345.4, dated Sep. 7, 2020 (pp. 14).
Office Action corresponding to Taiwanese application No. 108143986 dated Mar. 9, 2021. (pp. 7).
Search Report corresponding to Taiwanese application No. 108143986 dated Mar. 9, 2021. (pp. 2).
Gendeh et al (Biochemistry, 1997, 36, 11461-11471) (Year: 1997).
GenBank Document, 1996 (Year: 1996).
Taiwan Office Action and search report with English translation issued in corresponding TW Patent Application No. 111108172, dated Apr. 27, 2023, 8 pages.
S1 type peptidase, partial [Hapalochlaena maculosa] Protein—NCBI , retrieved from https://www.ncbi.nlm.nih.gov/protein/ACJ22651 on May 9, 2023, 1 page.

* cited by examiner

*Primary Examiner* — Sudhakar Katakam

(74) *Attorney, Agent, or Firm* — Muncy, Geissler, Olds & Lowe, P.C.

(57) ABSTRACT

The present disclosure provides peptides comprising a motif having four amino acids, wherein each of the amino acids at N-terminus and C-terminus of the sequence independently has a same or different positively charged side chain, and each of the amino acids between the N-terminal and C-terminal of the motif independently has a same or different uncharged side chain. The present disclosure surprisingly found that these peptides have advantageous effects in inhibiting or decreasing collagen breakdown, increasing production of collagen, elastin and/or hyaluronic acid, retarding aging, improving skin and inhibiting inflammation.

7 Claims, 12 Drawing Sheets

Specification includes a Sequence Listing.

BIOMIMETIC PEPTIDES DERIVED FROM BIOLOGICAL SOURCE AND THEIR USES IN RETARDING AGING AND IMPROVING SKIN

CROSS REFERENCE TO RELATED APPLICATIONS

This application is a Divisional of co-pending Application No. 16/702,385, filed on Dec. 3, 2019, which claims priority of U.S. Provisional Application No. 62/871,216 filed on 8 Jul. 2019 and U.S. Provisional Application No. 62/871,260 filed on 8 Jul. 2019 under 35 U.S.C. § 119(e), the entire contents of all of which are hereby incorporated by reference.

FIELD OF THE INVENTION

The present disclosure relates to peptides derived from a biological source. Particularly, the present disclosure relates to peptides having a specific motif and their applications such as inhibition or decrease of collagen breakdown, increase of production of collagen, elastin and/or hyaluronic acid, retardation of aging, improvement of skin and inhibition of inflammation.

BACKGROUND OF THE INVENTION

Aging is commonly defined as the accumulation of diverse deleterious changes occurring in cells and tissues with advancing age that are responsible for the increased risk of disease and death. The aging process is a dynamic and unchangeable phenomenon which affects all systems in the body. During the aging process, the dermis undergoes significant changes. Collagen, which is a major component of the extracellular matrix (ECM), becomes fragmented and coarsely distributed, and its total amount decreases.

Peptides have an important signal function and coordinate many biochemical processes; thus, peptides are widely applied in pharmaceutical and cosmetic industries. US 20180360720 is related to an anti-aging peptide, which has an amino acid sequence of ProAspSerThrGluAlaLys. US 20190153030 discloses peptides comprising from 3 to 10 amino acids including at least one peptide sequence K*(Ac)GH and cosmetic uses of said peptides. US 20190112336 provides a peptide consisting of 15 amino acids or less for skin regeneration or wound healing. US 20190040100 provides a peptide having activity to improve skin condition by inhibiting MMP2 activity.

There remains a need for the development of peptides capable of retarding aging.

SUMMARY OF THE INVENTION

In one aspect, the present disclosure provides a peptide or a salt thereof, comprising a sequence having four amino acids, wherein each of the amino acids at N-terminus and C-terminus of the sequence independently has a same or different positively charged side chain, and each of the amino acids between the N-terminal and C-terminal of the motif independently has a same or different uncharged side chain.

In one embodiment of the present disclosure, the sequence of the peptide is represented by Formula I: $X_1$-$X_2$-$X_3$-$X_4$ (SEQ ID NO:1), wherein $X_1$ is selected from an amino acid having a positively charged side chain; $X_2$ is selected from an amino acid having a uncharged side chain; $X_3$ is selected from an amino acid having an uncharged side chain; and $X_4$ is selected from an amino acid having a positively charged side chain. In some further embodiments, $X_1$ is K, R or H; $X_2$ and $X_3$ each independently is T, A I, C, S, G, Y, F, P or N; and $X_4$ is K, R or H. In some further embodiments, $X_1$ is K or R; $X_2$ and $X_3$ each independently is T, C, S, G, Y, I, F, P, N or A; and $K_4$ is K or R. In other embodiments, the sequence sets forth in SEQ ID NO:2 (RTCK), SEQ ID NO:3 (KSGR), SEQ ID NO:4 (KSGK), SEQ IDNO:5 (KYIK), SEQ ID NO:6 (KIFK), SEQ ID NO:7 (RPIK) or SEQ ID NO:8 (KNAK).

In some embodiments of the present disclosure, the sequence of Formula I further comprises one to four additional amino acid residues upstream to its N-terminus or downstream to its C-terminus.

In one embodiment, the sequence of Formula I further comprises one additional amino acid residue upstream to its N-terminus or downstream to its C-terminus, wherein the amino acid residue has an uncharged side chain. In a further embodiment, the amino acid residue is L, F or P. In a further embodiment, the sequence sets forth in SEQ ID NO:9 (LKSGR), SEQ ID NO:10 (KIFKF) or SEQ ID NO:11 (PRPIK).

In one embodiment, the sequence of Formula I further comprises one additional amino acid residue upstream to its N-terminus and one additional amino acid residue downstream to its C-terminus, wherein the additional amino acid residue has an uncharged side chain. In a further embodiment, the amino acid residue is T, F, V or Y In another embodiment, the sequence sets forth in SEQ ID NO:12 (TKSGKF) or SEQ ID NO:13 (VKNAKY).

In one embodiment, the sequence of Formula I further comprises three additional amino acid residues upstream to its N-terminus, wherein, from the 5' to 3' direction, the first is the amino acid residue having an uncharged side chain and the second and the third are amino acid residues having a positively charged side chain. In a further embodiment, the amino acid residue having an uncharged side chain is Q and the amino acid residues having a positively charged side chain are each independently K or R. In yet another embodiment, the sequence sets forth in SEQ ID NO:14 (QKRRTCK).

In one embodiment, the sequence of Formula I further comprises three additional amino acid residues upstream to its N-terminus and one additional amino acid residue downstream to its C-terminus, wherein the amino acid residues have an uncharged side chain. In a further embodiment, the amino acid residues having an uncharged side chain are each independently Q, R, I or P. In another embodiment, the sequence sets forth in SEQ ID NO:15 (QRIKYIKP).

In some further embodiments, the peptide comprises a sequence selected from a group consisting of SEQ ID NOs: 2 to 15.

In the present disclosure, the peptide may be a D-form or L-form peptide, or a peptide in which only a portion of the sequence consists of a D-form or L-form peptide or a racemic form thereof.

In another aspect, the present disclosure provides a composition comprising a peptide of the present disclosure and at least one carrier, diluent, or excipient. In some embodiments, the composition is a pharmaceutical composition, cosmetic composition or a dietary supplement. In one embodiment, the cosmetic composition is a solution used in face mask.

In another aspect of the present disclosure, the present disclosure provides a method for inhibiting or decreasing collagen breakdown and/or increasing collagen synthesis in a subject, comprising administering or applying the peptide of the present disclosure to the subject. In one embodiment, the collagen is collagen I and/or collagen IV. In another embodiment, the peptide can inhibit expression of matrix metallopeptidase-1.

In another aspect, the present disclosure provides a method for increasing production of elastin and/or hyaluronic acid in a subject, comprising administering or applying the peptide of the present disclosure to the subject.

In yet another aspect, the present disclosure provides a method for retarding aging in a subject, comprising administering or applying the peptide of the present disclosure to the subject.

In one embodiment, the peptide can increase production of telomerase, improve DNA repair and/or increase anti-oxidation effect.

In one embodiment, the peptide can increase expression of anti-aging genes. In another embodiment, the peptide can increase production of superoxide dismutase (SOD) and/or hyaluronic acid synthase.

In a different embodiment, the peptide can increase expression of moisture-retention related genes.

In a further aspect of the disclosure, the present disclosure provides a method for improving skin, comprising administering or applying the peptide of the present disclosure to the subject. In one embodiment, the improvement of skin includes repairing skin defects. Examples of the skin defects include but are not limited to: poor skin texture, wrinkles, fine lines, UV induced skin damage, skin aging, dry skin, hair follicle deterioration, alopecia, dermatitis, eczema, rash, pruritus, sun burn, burns, stretch marks, acne scars, surgical scars, depleted collagen levels, depleted elastin levels, skin sagging, diabetic neuropathies, hardened-cracked skin and hardened cracked heel tissue.

In yet another aspect, the present disclosure provides a method for inhibiting inflammation in a subject, comprising administering or applying the peptide of the present disclosure to the subject.

DETAILED DESCRIPTION OF THE INVENTION

Figure 1:
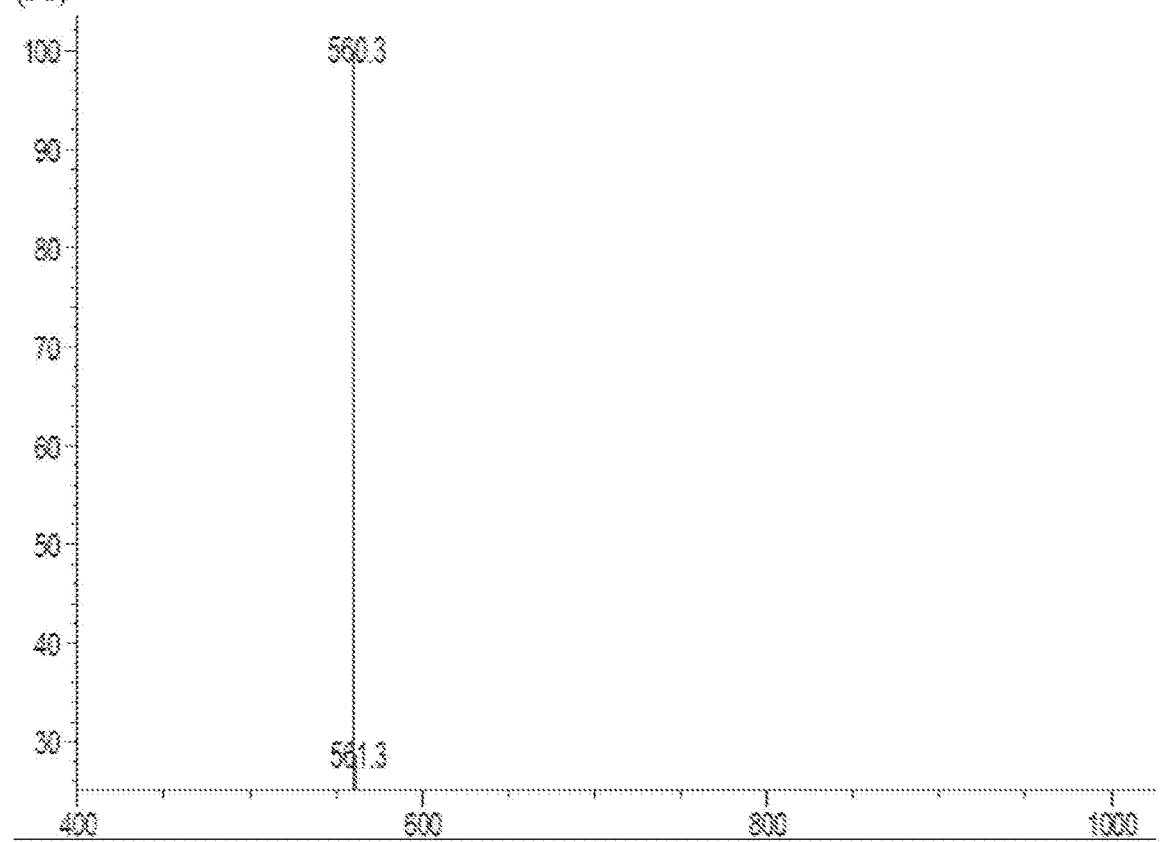
FIG. 1 (A) to (G) show the mass spectrums of Latrol-5 (A), Latrol-6 (B), Hapa-5 (C), Hapa-6 (D), Chiro-5 (E), Chiro-8 (F) and Heter-7 (G).
Figure 1:
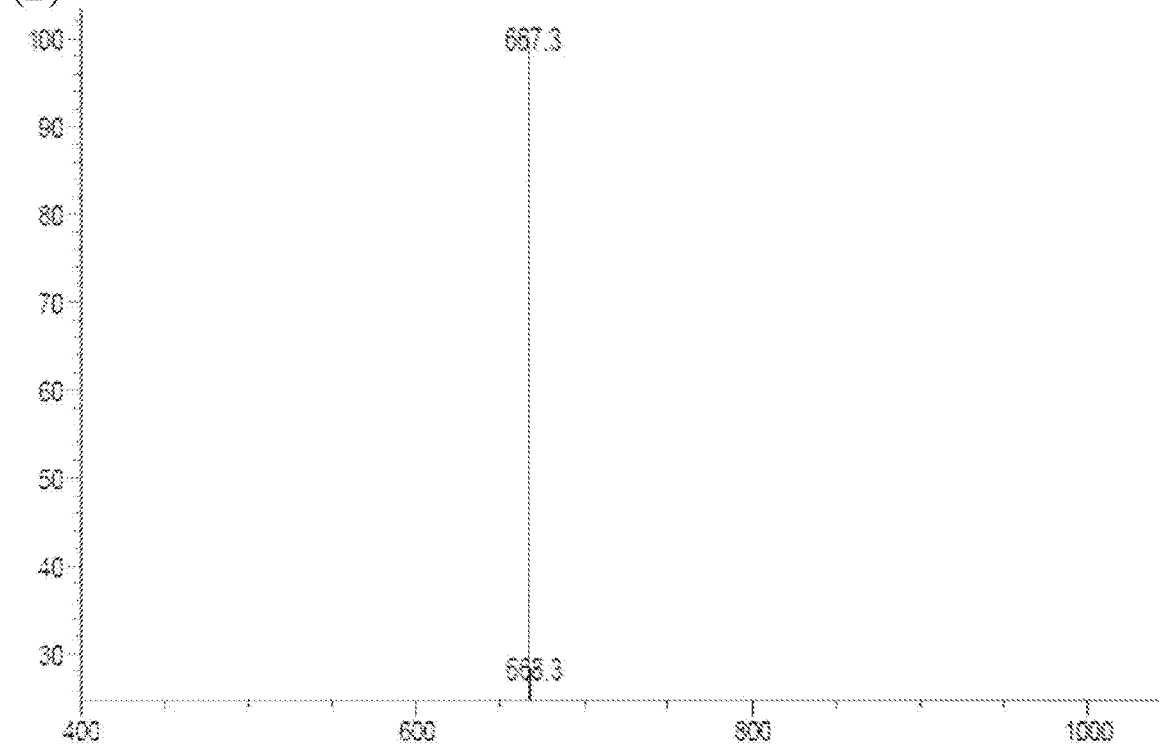
Figure 1:
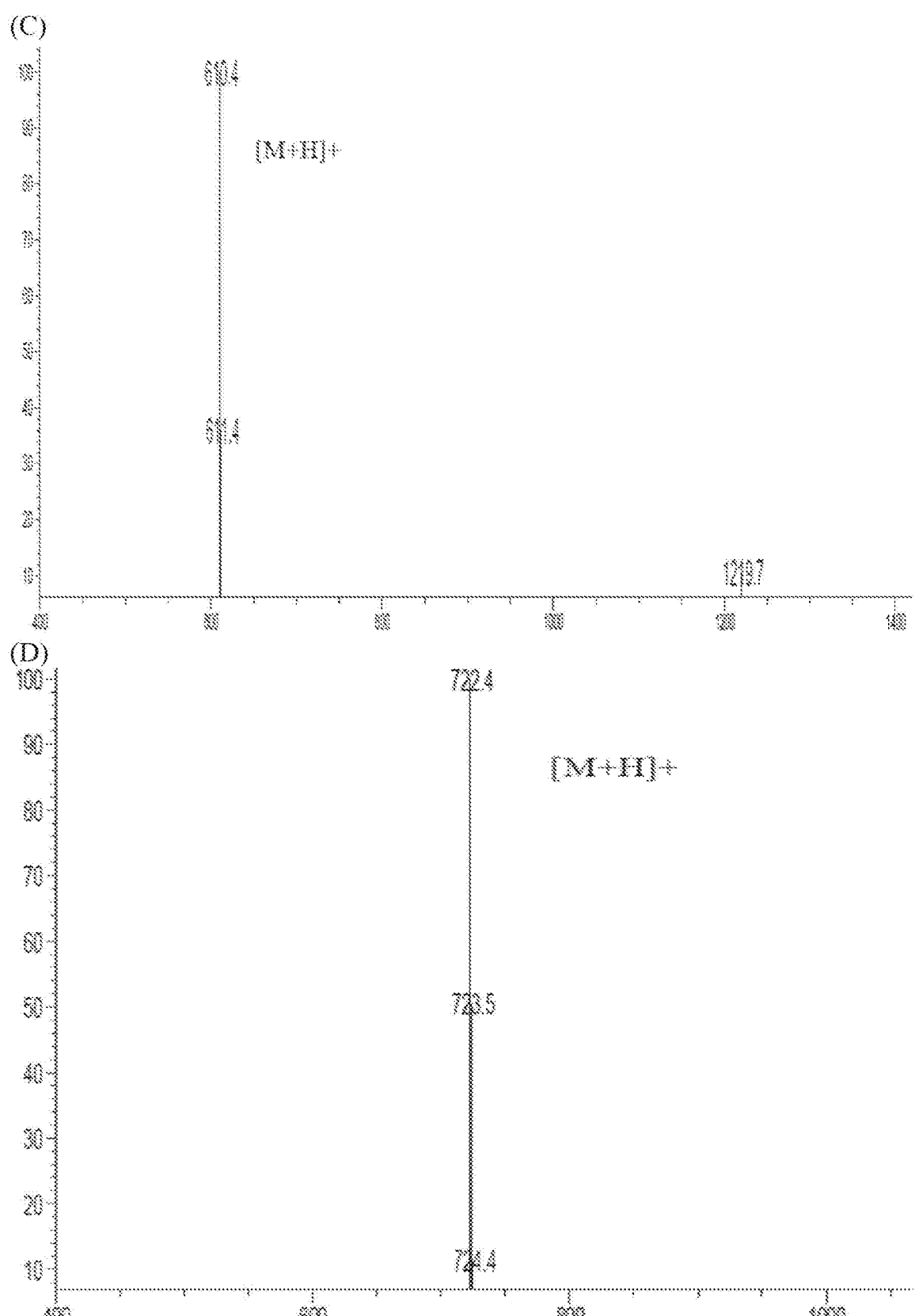
Figure 1:
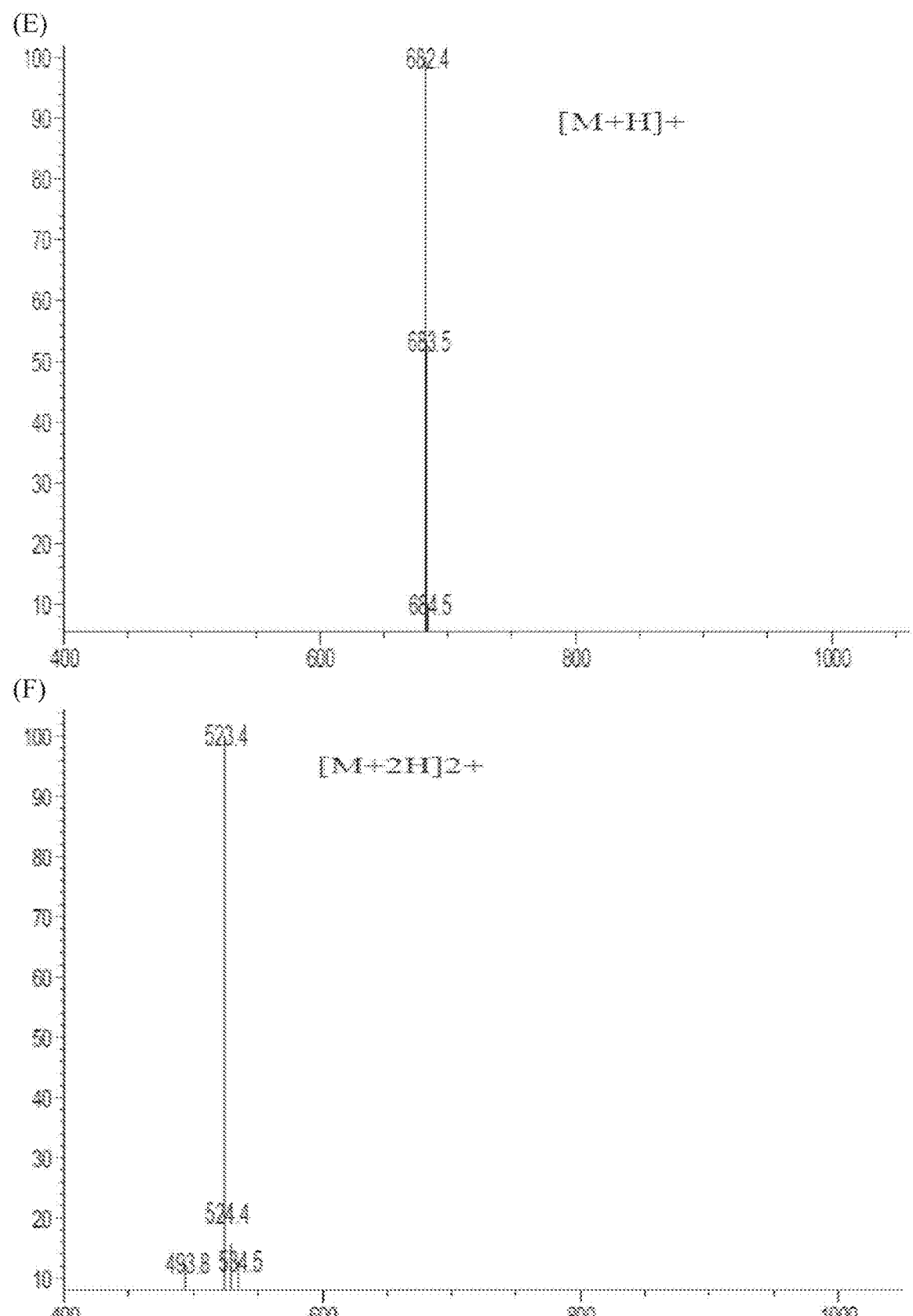
Figure 1:
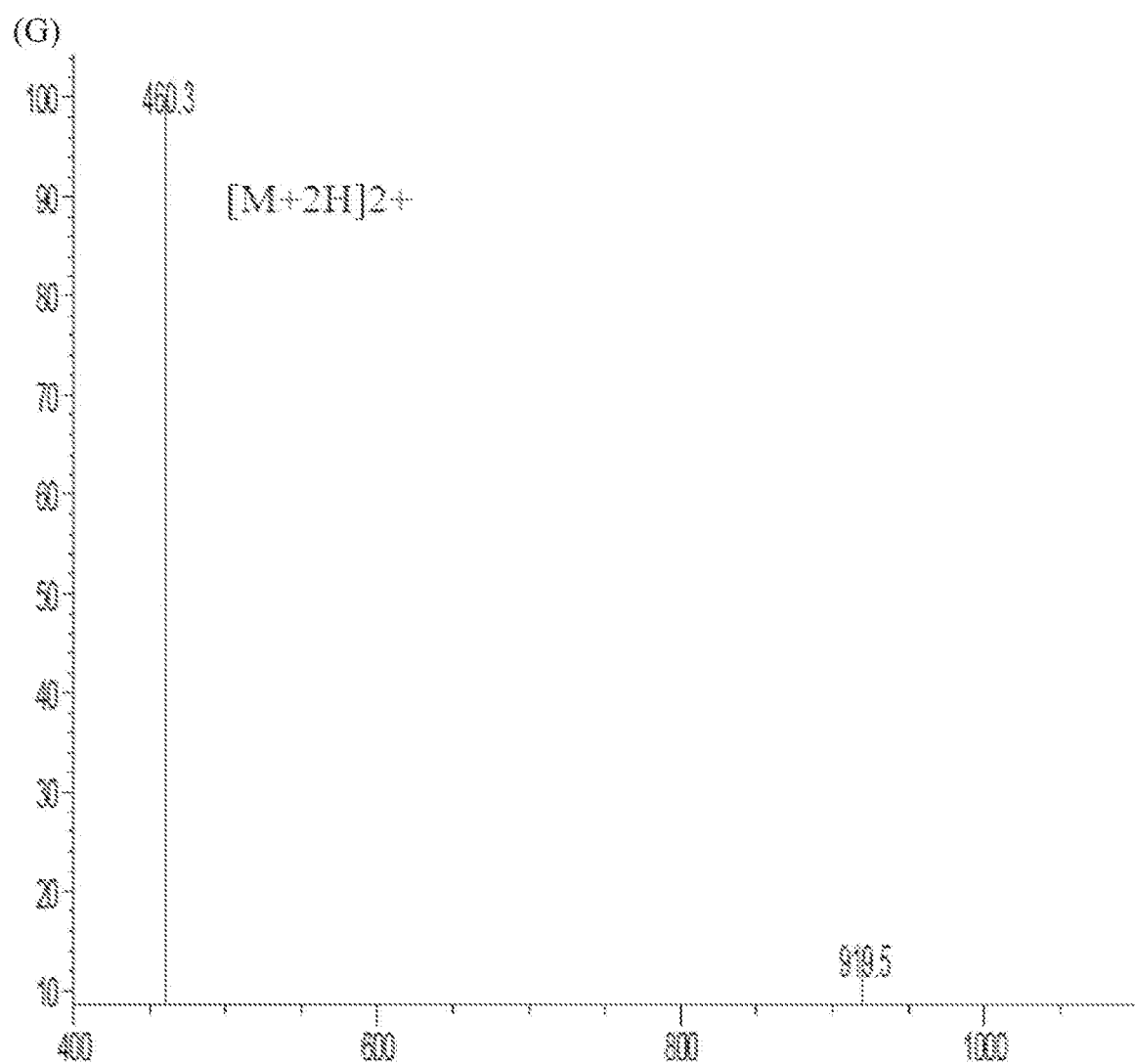

Unless otherwise defined, all technical and scientific terms used herein have the same meaning as commonly understood by one of ordinary skill in the art. Although methods and materials similar or equivalent to those described herein can be used in the practice or testing of the present invention, suitable methods and materials are described below. All publications, patent applications, patents, and other references mentioned herein are incorporated by reference in their entirety. In addition, the materials, methods, and examples are illustrative only and not intended to be limiting.

Definitions

The singular forms "a", "and", and "the" are used herein to include plural referents unless the context clearly dictates otherwise.

The phrase "and/or," as used herein, should be understood to mean "either or both" of the elements. As used herein, "or" should be understood to have the same meaning as "and/or" as defined above.

As used herein, a "peptide" refers to a single-chain polyamide containing a plurality of amino acid residues, such as naturally-occurring and/or non-natural amino acid residues, that are consecutively bound by amide bonds. Examples of peptides include shorter fragments of full-length proteins, such as full-length naturally-occurring proteins. Amino acids are well known in the art and include, for example: isoleucine, leucine, alanine, asparagine, glutamine, lysine, aspartic acid, glutamic acid, methionine, cysteine, phenylalanine, threonine, tryptophan, glycine, valine, proline, serine, tyrosine, arginine, histidine, norleucine, ornithine, taurine, selenocysteine, selenomethionine, lanthionine, 2-aminoisobutyric acid, dehydroalanine, hypusine, citrulline, 3-aminopropanoic acid, gamma-aminobutyric acid, nitroarginine, N-methylated leucine, homoarginine, dimethyl arginine, acetyl lysine, azalysine, pyrrolysine, and the like. An "amino acid side chain" refers to the various organic substituent groups that differentiate one amino acid from another. An amino acid having a hydrophobic uncharged side chain includes the non-limiting examples of alanine (A), isoleucine (I), leucine (L), methionine (M), phenylalanine (F), tryptophan (W), tyrosine (Y), and valine (V). An amino acid having a polar uncharged side chain includes the non-limiting examples of serine (S), threonine (T), asparagine (N), and glutamine (Q). An amino acid having a positively charged side chain, under typical physiological conditions, includes the non-limiting examples of arginine (R), histidine (H), and lysine (K). An amino acid having a negatively charged side chain, under typical physiological conditions, includes the non-limiting examples of aspartic acid (D) and glutamic acid (E). A "derivative" of an amino acid side chain refers to an amino acid side chain that has been modified structurally (e.g., through chemical reaction to form new species, covalent linkage to another molecule, and the like).

As used herein, the term "amino acid residue" may be derived from natural or non-natural alpha-amino acid and may be either an L form or a D form in a case where there may be an optical active material, but an L form is preferable.

As used herein, the terms "subject," "individual" and "patient" are interchangeable and refer to an organism that receives an application or treatment for a particular disease or condition as described herein.

As used herein, the term "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, the term "dermatologically acceptable," as used herein, means that the compositions or components described are suitable for use in contact with human skin tissue.

As used herein, the term "effective amount" of an agent in the context of administration, refers to an amount effective, at dosages/amounts and for periods of time necessary, to achieve a desired result.

As used herein, the term "therapeutically effective amount" of an agent refers to an amount effective, at dosages and for periods of time necessary, to achieve a desired therapeutic result, such as for treatment of a disease, condition, or disorder, and/or pharmacokinetic or pharmacodynamic effects of the treatment.

Peptides of the Present Disclosure

The present invention provides synthetic peptide derived from poison proteins from jelly fish (such as *Chironex fleckeri*), sea anemone (such as *Heteractis magnifica*), spider (such as *Latrodectus mactans*) or octopus (such as *Hapalochlaena maculosa*). The synthetic peptide of the present disclosure comprises an amino acid sequence, which may be naturally occurring, or peptide mimetics, peptide analogs and/or synthetic derivatives of four amino acids (4-mer), five amino acids (5-mer), six amino acids (6-mer), seven amino acids (7-mer) or eight amino acids (8-mer).

The present disclosure surprisingly found that the peptides comprising a motif having four amino acids have advantageous effects in inhibiting or decreasing collagen breakdown, increasing production of collagen, elastin and/or hyaluronic acid, retarding aging, improving skin and inhibiting inflammation. In the motif having four amino acids, each of the lo amino acids at N-terminus and C-terminus of the sequence independently has a same or different positively charged side chain and each of the amino acids between the N-terminal and C-terminal of the motif independently has a same or different uncharged side chain.

In one embodiment, the 4-mer motif sequence has the following Formula I: $X_1$-$X_2$-$X_3$-$X_4$ (SEQ ID NO:1), wherein $X_1$ is selected from an amino acid having a positively charged side chain; $X_2$ is selected from an amino acid having a uncharged side chain; $X_3$ is selected from an amino acid having an uncharged side chain; and $X_4$ is selected from an amino acid having a positively charged side chain. Preferably, $X_1$ is K, R or H; $X_2$ and $X_3$ each independently is T, A I, C, S, G, Y, F, P or N; and $K_4$ is K, R or H. In some further embodiments, $X_1$ is K or R; $X_2$ and $X_3$ each independently is T, C, S, G, Y, I, F, P, N or A; and $K_4$ is K or R. In other embodiments, the sequence sets forth in SEQ ID NO:2 (RTCK), SEQ ID NO:3 (KSGR), SEQ ID NO:4 (KSGK), SEQ IDNO:5 (KYIK), SEQ ID NO:6 (KIFK), SEQ ID NO:7 (RPIK) or SEQ ID NO:8 (KNAK).

Furthermore, the 4-mer motif sequence can further comprise one to four additional amino acid residues upstream to its N-terminus or downstream to its C-terminus to form a 5-mer, 6-mer, 7-mer or 8-mer motif sequence.

To form a 5-mer motif sequence, one additional amino acid residue can be added to the 4-mer motif sequence at upstream to its N-terminus or downstream to its C-terminus. Preferably, the additional amino acid residue has an uncharged side chain. In some embodiments, the amino acid residue is L, F or P. In a further embodiment, the sequence sets forth in SEQ ID NO:9 (LKSGR), SEQ ID NO:10 (KIFKF) or SEQ ID NO:11 (PRPIK).

To form a 6-mer motif sequence, the 4-mer motif sequence further comprises one additional amino acid residue upstream to its N-terminus and one additional amino acid residue downstream to its C-terminus. Preferably, the additional amino acid residue has an uncharged side chain. In some embodiments, the amino acid residue is T, F, V or Y. In a further embodiment, the sequence sets forth in SEQ ID NO:12 (TKSGKF) or SEQ ID NO:13 (VKNAKY).

To form a 7-mer motif sequence, the 4-mer motif sequence further comprises three additional amino acid residues upstream to its N-terminus, wherein, from the 5' to 3' direction, the first is the amino acid residue having an uncharged side chain, and the second and the third are amino acid residues having a positively charged side chain. Preferably, the amino acid residue having an uncharged side chain is Q, and the amino acid residues having a positively charged side chain are each independently K or R. In some embodiments, the sequence sets forth in SEQ ID NO:14 (QKRRTCK).

To form a 8-mer motif sequence, the 4-mer motif sequence further comprises three additional amino acid residues upstream to its N-terminus and one additional amino acid residue downstream to its C-terminus, wherein the amino acid residues have an uncharged side chain. In some embodiments, the amino acid residues having an uncharged side chain are each independently Q, R, I or P. In a further embodiment, the sequence sets forth in SEQ ID NO:15 (QRIKYIKP).

The peptide may be a D-form or L-form peptide, or a peptide, only a portion of the sequence of which consists of a D-form or L-form peptide, or a racemic form thereof.

Substitutes for an amino acid within the peptide sequence may be selected from other members of the class to which the amino acid belongs. For example, the nonpolar (hydrophobic) amino acids include: alanine, leucine, isoleucine, valine, proline, phenylalanine, tryptophan, and methionine. Amino acids containing aromatic ring structures include: phenylalanine, tryptophan, and tyrosine. The polar neutral amino acids include: glycine, serine, threonine, cysteine, tyrosine, asparagine, and glutamine. The positively charged (basic) amino acids include arginine and lysine. The negatively charged (acidic) amino acids include aspartic acid and glutamic acid.

The structure of the N-terminal of the peptide according to the present disclosure is not particularly limited, and for example, may be a structure of a hydrogen atom (that is, unmodified) or a structure in which a modifying group is introduced by a conventionally known method. The structure of the C-terminal of the peptide according to the present disclosure is also not particularly limited, and may be a structure which is modified by a protective group generally used for protection of a carboxylic acid.

The amino acid sequences described herein are described in accordance with the conventional denotation in a direction from the N-terminal (amino terminal) side to the C-terminal (carboxyl terminal) side unless otherwise noted.

The peptide according to the present invention can be produced by conventionally known methods including a chemical synthesis method and a recombinant technique. For producing the peptide by chemical synthesis, the peptide can be produced by a method of usually using each amino acid in peptide chemistry. The peptide can also be produced by any one of a liquid-phase method and a solid-phase method. Further, any method of a column method and a batch method can also be used.

The peptide according to the present disclosure may also be produced, for example, by a method as described in Current Protocols in Molecular Biology, or a recombinant technique using animal cells, insect cells, microorganisms, or the like. The peptide is generated by cultured cells or microorganisms and then may be purified by a conventionally known method. The purification and isolation method of the peptide is known in the field.

Compositions and Applications

The peptides according to the present disclosure can increase production of collagen, inhibit expression of matrix metallopeptidase-1, increase production of telomerase, improve DNA repair, increase production of superoxide dismutase (SOD) and/or hyaluronic acid synthase, increase anti-oxidation effect and/or increase expression of anti-aging genes, collagen genes and/or elastin genes. Accordingly, the peptides of the present disclosure can inhibit or decrease collagen breakdown and/or increase collagen synthesis, increase production of elastin and/or hyaluronic acid, retard aging, improve skin and/or inhibit inflammation.

In the aspect of improving skin, the improvement includes repairing skin defects. Examples of skin defects include, but are not limited to: poor skin texture, wrinkles, fine lines, UV induced skin damage, skin aging, dry skin, hair follicle deterioration, alopecia, dermatitis, eczema, rash, pruritus, sun burn, burns, stretch marks, acne scars, surgical scars, depleted collagen levels, depleted elastin levels, skin sagging, diabetic neuropathies, hardened-cracked skin and hardened cracked heel tissue.

The peptides according to the present disclosure can be formulated as a composition with at least one carrier, diluent, or excipient. The composition can be a pharmaceutical composition, cosmetic composition or a dietary supplement.

For pharmaceutical composition, pharmaceutically acceptable carriers, excipients and diluents are incorporated, which are familiar to those skilled in the art. For compositions formulated as liquid solutions, acceptable carriers and/or diluents include saline and sterile water, and may optionally include antioxidants, buffers, bacteriostats and other common additives. The compositions can also be formulated as pills, capsules, granules, or tablets which contain—in addition to a compound of the invention—diluents, dispersing and surface active agents, binders, and lubricants. One skilled in this art may further formulate the compound of the invention in an appropriate manner, and in accordance with accepted practices, such as those disclosed in Remington's Pharmaceutical Sciences, Gennaro, Ed., Mack Publishing Co., Easton, Pa. 1990. In some embodiments, peptides of the present disclosure may be administered topically, (intra)dermally, or transdermally to the skin or mucosa. Typical formulations include: gels, hydrogels, lotions, solutions, creams, ointments, dressings, foams, skin patches, wafers, implants and microemulsions. Compounds of the present invention may also be administered via inhalation or intranasal administration, such as with a dry powder, an aerosol spray or as drops. Additional routes of administration for compounds of the present invention include intravaginal and rectal (by means of a suppository, pessary or enema), and ocular and aural.

The peptides of the present disclosure may be included in any formulation suitable for application to the skin. Dermatologically acceptable carriers should be safe for use in contact with human skin tissue. Suitable carriers may include water and/or water miscible solvents. Suitable water miscible solvents include: monohydric alcohols, dihydric alcohols, polyhydric alcohols, glycerol, glycols, polyalkylene glycols such as polyethylene glycol, and mixtures thereof. When the skin care composition is in the form of an emulsion, water and/or water miscible solvents are carriers typically associated with the aqueous phase. Suitable carriers also include oils, which may be used to solubilize, disperse, or carry materials that are not suitable for water or water soluble solvents. Suitable oils include silicones, hydrocarbons, esters, amides, ethers, and mixtures thereof. The oils may be volatile or nonvolatile.

The peptides of the present disclosure may be formulated as: a topical composition in the form of an ointment, a cream, a lotion, a liniment or other spreadable liquid or semi liquid preparation, a solution, a dispersion, an emulsion such as micro-emulsion, oil-in-water emulsion or water-in-oil emulsion, a suspension, a gel, liposomes, a sprayable composition, an aerosol, a film, powders, washes, shampoos etc. In one embodiment, the cosmetic formulation is a solution used in face mask.

As mentioned above, the composition may be in the form of an emulsion. Creams and lotions are normally examples of compositions that are in the form of an emulsion. An emulsion is a dispersed system comprising at least two immiscible liquid phases (an oil phase and an aqueous phase), one phase dispersed in the other. An emulsifying agent is typically included to improve physical stability.

As mentioned above, the composition may be in the form of a suspension. Examples of suspensions are dispersions, ointments, liniments, sprays and aerosols.

As mentioned above, the composition may be in the form of a gel or hydrogel. A gel typically contains a swellable polymer like cellulose or cellulose derivatives (as those previously mentioned herein), pectin, alginate, tragacant, carbomer, polyvinyl alcohols, gelatin, acrylate-based polymers etc.

As mentioned above, the composition may be in the form of an ointment, which is an oleaginous semisolid that contains little if any water. Normally, an ointment has a hydrocarbon base such as wax, petrolatum or gelled mineral oil.

A composition of the invention may also contain one or more additive such as pH adjusting agents, buffering agents, viscosity-adjusting agents, aromas, anti-oxidants, moisturizers, preservatives, stabilizers etc.

EXAMPLES

While the following examples provide further detailed description of certain aspects and embodiments of the disclosure, they should be considered merely illustrative and not in any way limiting to the scope of the claims.

Example 1 Preparation of Peptides of the Present Disclosure

Fmoc solid-phase peptide synthesis was used to prepare the peptides of the present disclosure. Fmoc chemistry is well known in the art, which was developed by Eric Atherton and Bob Sheppard at the Laboratory of Molecular Biology in Cambridge in the late 1970's, and has been reviewed by Chan and White (Fmoc Solid Phase Peptide Synthesis—A Practical Approach. Oxford University Press, 2000).

The following Fmoc amino acids were employed for Latrol-5 (LKSGR; SEQ ID NO:9): Fmoc-Arg(pbf)-OH, Fmoc-Gly-OH, Fmoc-Ser-OH, Fmoc-Lys(Boc)-OH and Fmoc-Leu-OH.

The following Fmoc amino acids were employed for Latrol-6 (TKSGKF; SEQ ID NO:12): Fmoc-Phe-OH, Fmoc-Lys(Boc)-OH, Fmoc-Gly-OH, Fmoc-Ser-OH, Fmoc-Lys(Boc)-OH and Fmoc-Thr-OH.

The following Fmoc amino acids were employed for Hapa-5 (PRPIK; SEQ ID NO:11): Fmoc-Lys(Boc)-OH, Fmoc-Ile-OH, Fmoc-Pro-OH, Fmoc-Arg(pbf)-OH and Fmoc-Pro-OH.

The following Fmoc amino acids were employed for Hapa-6 (VKNAKY; SEQ ID NO:13): Fmoc-Tyr(But)-OH, Fmoc-Lys(Boc)-OH, Fmoc-Ala-OH, Fmoc-Asn(Trt)-OH, Fmoc-Lys(Boc)-OH and Fmoc-Val-OH.

The following Fmoc amino acids were employed for Chiro-5 (KIFKF; SEQ ID NO:10): Fmoc-Phe(Boc)-OH, Fmoc-Lys(Boc)-OH, Fmoc-Phe(Boc)-OH, Fmoc-Ile-OH, and Fmoc-Lys(Boc)-OH.

The following Fmoc amino acids were employed for Heter-7 (QKRRTCK; SEQ ID NO:14): Fmoc-Lys(Boc)-OH, Fmoc-Cys(Trt)-OH, Fmoc-Thr-OH, Fmoc-Arg(pbf)-OH, Fmoc-Arg(pbf)-OH, Fmoc-Lys(Boc)-OH and Fmoc-Glu(O-t-Bu)-OH.

The following Fmoc amino acids were employed for Chiro-8 (QRIKYIKP; SEQ ID NO:15): Fmoc-Pro-OH, Fmoc-Lys(Boc)-OH, Fmoc-Ile-OH, Fmoc-Tyr(But)-OH, Fmoc-Lys(Boc)-OH, Fmoc-Ile-OH, Fmoc-Arg(pbf)-OH and Fmoc-Glu(O-t-Bu)-OH.

Fmoc removal was executed using a solution of piperidine in dimethylformamide (DMF) at room temperature for 30 min. Coupling of Fmoc protected amino acid units was carried out by activation with (O-(7-azabenzotriazol-1-yl)-N,N,N',N'-tetramethyluronium hexafluorophosphate (HATU) using 1-Methyl-2-pyrrolidinone (NMP) at room temperature for 40 min.

The Fmoc amino acids (1 g), HATU (1 g in NMP) and N,N-Diisopropylethylamine (DIEA) (3 mol/L) were subsequently mixed with the resin manually. This procedure was repeated twice for each coupling. Upon completion of synthesis, the peptide resin was subjected to a cleavage cocktail for 2 h. The resin was filtered and the combined filtrates were blown off under a stream of condensed air. The crude product was triturated with cold diethyl ether to give a white suspension which was centrifuged, and the ether subsequently decanted. The remaining solid was subjected to HPLC purification using C18 column (Gemini-NX C-18 110 Å (Phenomenex, 250×4.6 mm, 5 μm)), buffer solution A (0.1% TFA in 100% water) and buffer solution B (0.1% TFA in ACN). The elution rate at 1.0 ml/min and 30 minutes of elution time were used in the HPLC purification. The peptides were detected using Hitachi 5410 UV detector at a wavelength of 210~280 nm. The resulting purified peptides have purity of more than 95%. The purified peptides were then subjected to Mass Spectrometer (Agilent-6125B system) and the results are shown in FIG. 1 (A) to (G).

Example 2 Assay in Increasing Expression of Genes

A human fibroblast cell line (CCD-966SK) was used to assay gene expression affected by the peptides of the present disclosure. 1×10$^5$ of fibroblast cells were seeded and cultured in a 6-well plate containing 2 ml of X-VIVO™ 10 medium. The peptides (12.5 μg/ml and 25 μg/ml), Hapa-5, Hapa-6, Latrol-5, Latrol-6, Chiro-5, Chiro-8 and Heter-7 were added to the plate and then the resulting cell mixtures were cultured with the peptides for 6 or 24 hours, respectively. The cells cultured with the medium only for 6 or 24 hours were used as control.

The resulting cultured cells were washed with PBS and lysed by adding a lysis reagent. The resulting cell lysis solutions were extracted by RNA Extraction Kit (GENEzol™ 96 Well TriRNA Pure Kit, Geneaid) to collect the RNAs in the cells. The expression of genes was detected by the nCounter Analysis System (NanoString Technologies, Inc.)

Figure 2:
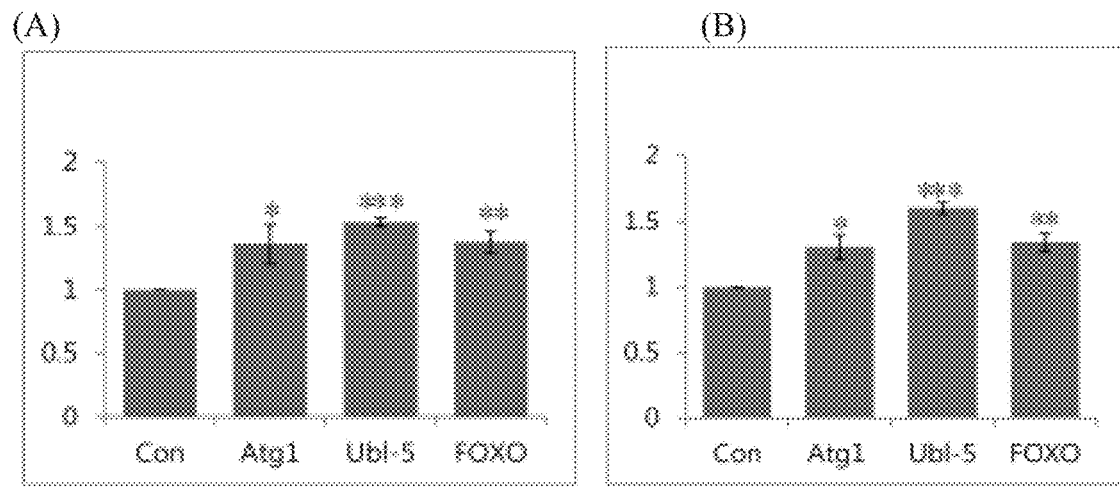
FIGS. 2 (A) and (B) show that in comparison with control (Con), Hapa-5 (25 μg/ml) (A) and Hapa-6 (12.5 μg/ml) (B) increase the expression of anti-aging genes (Atg1, Ub1-5 and FOXO) in 24 hours and 6 hours, respectively.
Figure 3:
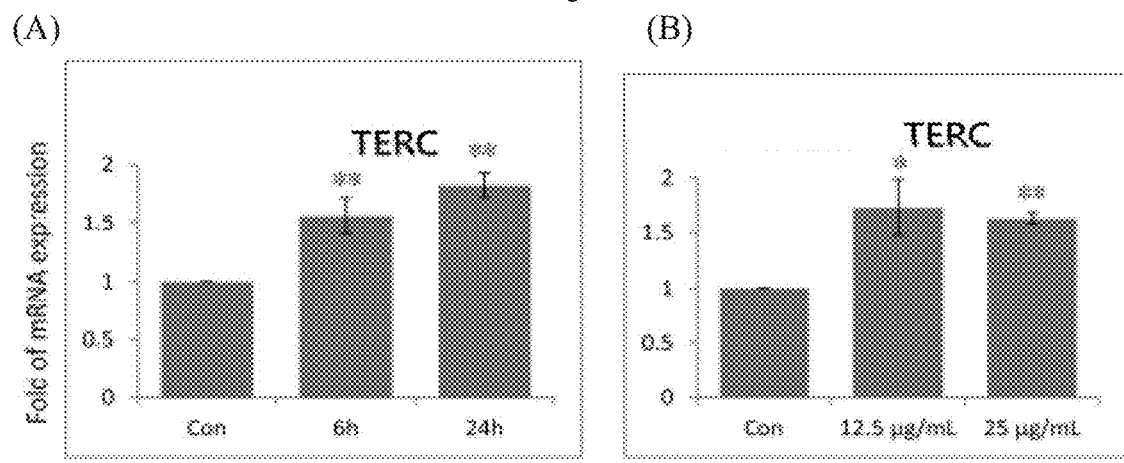
FIGS. 3 (A) and (B) show that in comparison with control (Con), Hapa-5 (12.5 μg/ml) (A) and Hapa-6 (12.5 and 25 μg/ml) (B) increase the expression of telomerase genes (TERC) in 24 hours.
Figure 4:
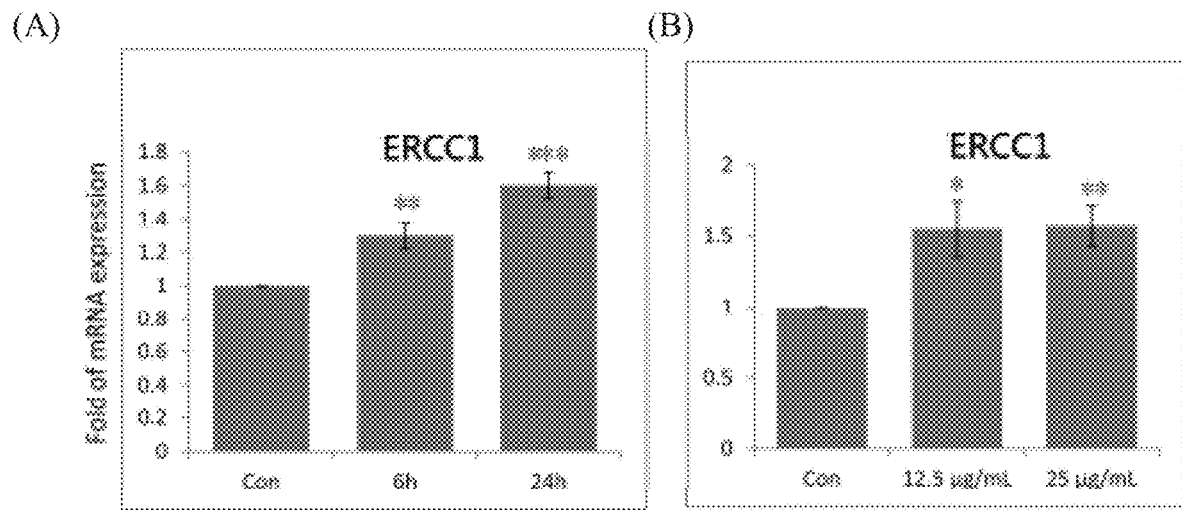
FIGS. 4 (A) and (B) show that in comparison with control (Con), Hapa-5 (12.5 μg/ml) (A) and Hapa-6 (12.5 and 25 μg/ml) (B) increase the expression of DNA repair genes (ERCC1) in 24 hours and 6 hours, respectively.
Figure 5:
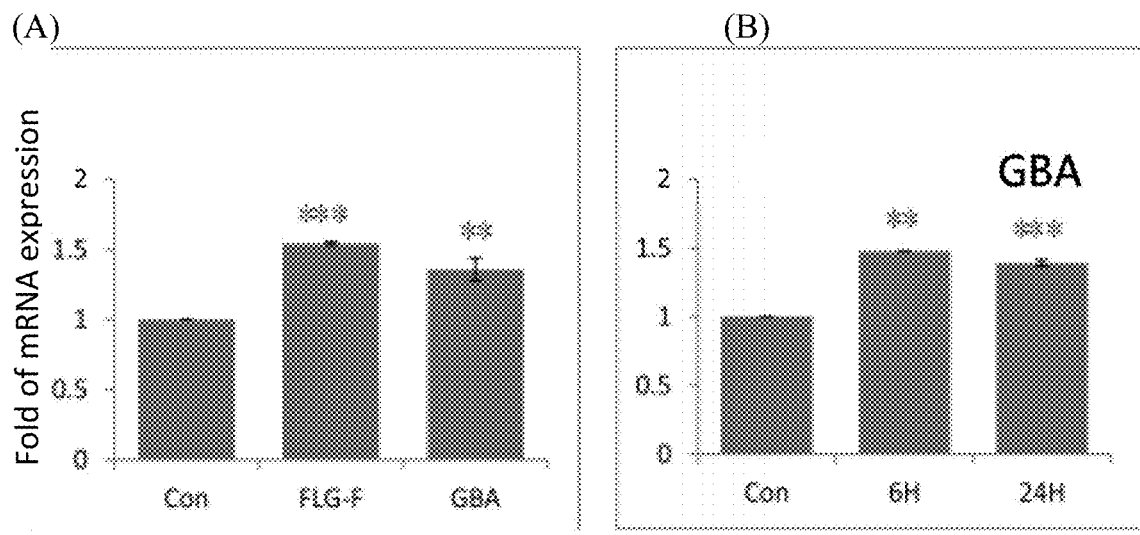
FIGS. 5 (A) and (B) show that in comparison with control (Con), Hapa-5 (A) and Hapa-6 (25 μg/ml) (B) increase the expressions of moisture-retention related genes (ELG-F and GBA).
Figure 6:
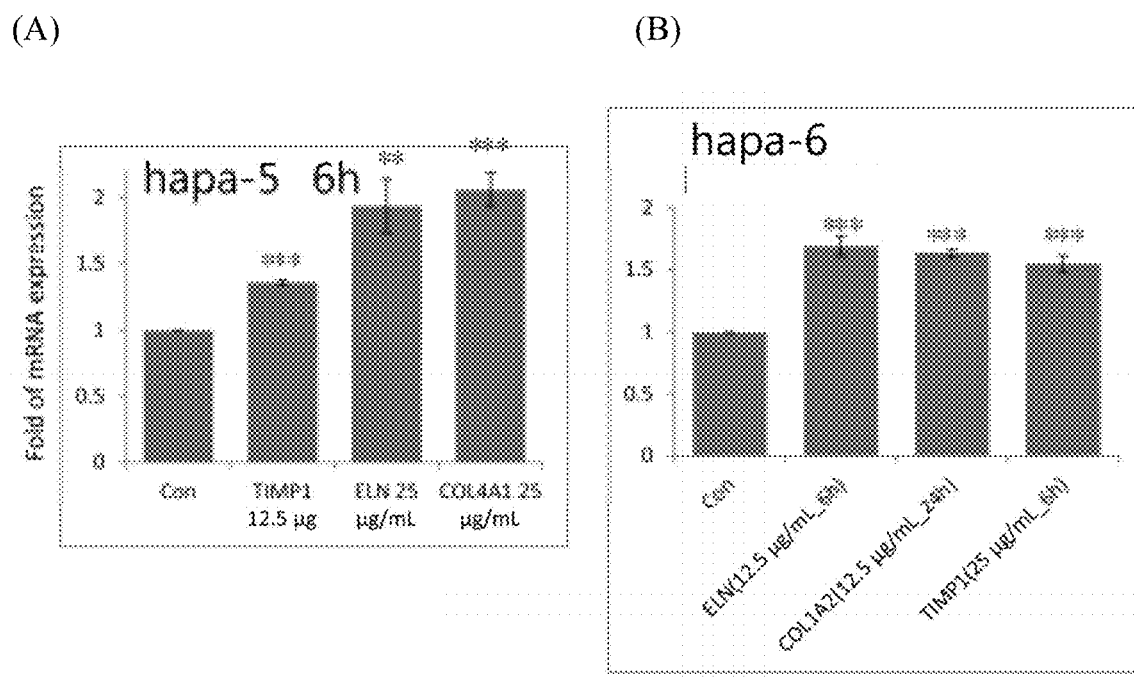
FIGS. 6 (A) and (B) show that in comparison with control (Con), Hapa-5 (A) increases the expression of collagen IV genes (COL4A1), elastin genes (ELN) and TIMP1 in 6 hours and Hapa-6 (B) increase the expression of collagen I genes (COL1A2) in 24 hours, elastin genes (ELN) in 6 hours and TIMP1 in 6 hours, respectively.
Figure 7:
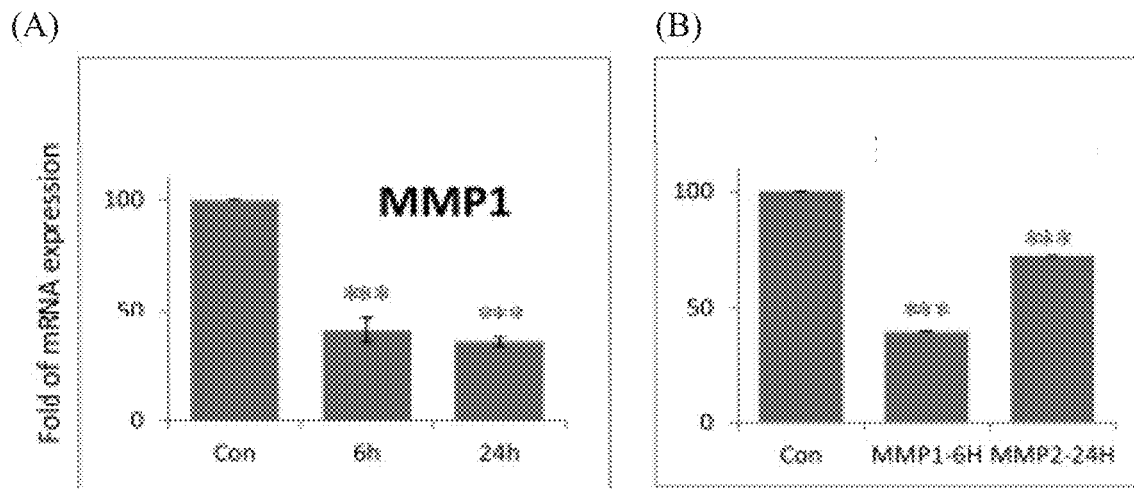
FIGS. 7 (A) and (B) show that in comparison with control (Con), Hapa-5 (25 μg/ml) (A) and Hapa-6 (12.5 μg/ml) (B) inhibits the expression of genes relating to collagen breakdown (MMP-1) in 24 hours.

The results show that Hapa-5 and Hapa-6 increase the expression of anti-aging genes (Atg1, Ubl-5 and FOXO) (FIG. 2 (A) and (B)), the expression of telomerase genes (TERC) (FIG. 3 (A) and (B)), the expression of DNA repair genes (ERCC1) (FIG. 4 (A) and (B)), the expression of moisture-retention related genes (ELG-F and GBA) (FIG. 5 (A) and (B)) and the expression of collagen I gene (Hapa-6) or collagen IV gene (Hapa-5), elastin genes and TIMP1 (FIG. 6 (A) and (B)). Moreover, Hapa-5 and Hapa-6 inhibits the expression of genes relating to collagen breakdown (MMP-1) (FIG. 7 (A) and (B)).

Figure 8:
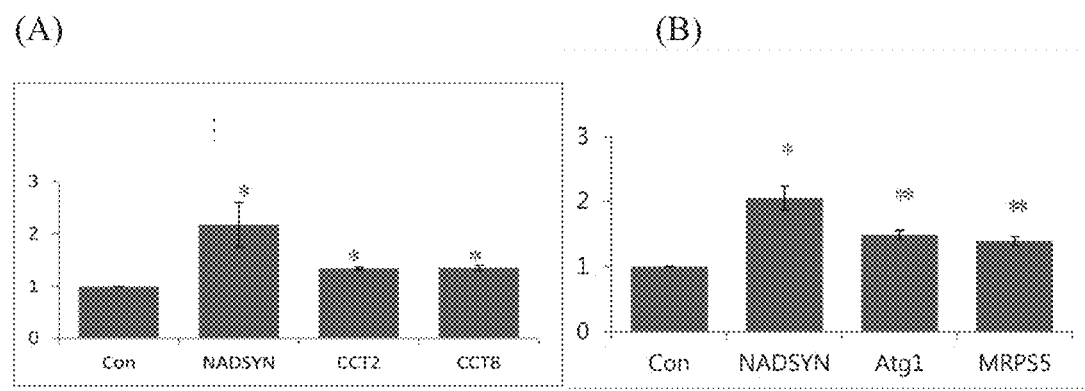
FIGS. 8 (A) and (B) show that in comparison with control (Con), Latrol-5 (25 μg/ml) increases the expression of anti-aging genes (NADSYN, CCT2 and CCT8) in 6 hours (A) and Latrol-6 (25 μg/ml) increases the expression of anti-aging genes (NADSYN, Atg1, MRPS5) in 24 hours (B).
Figure 9:
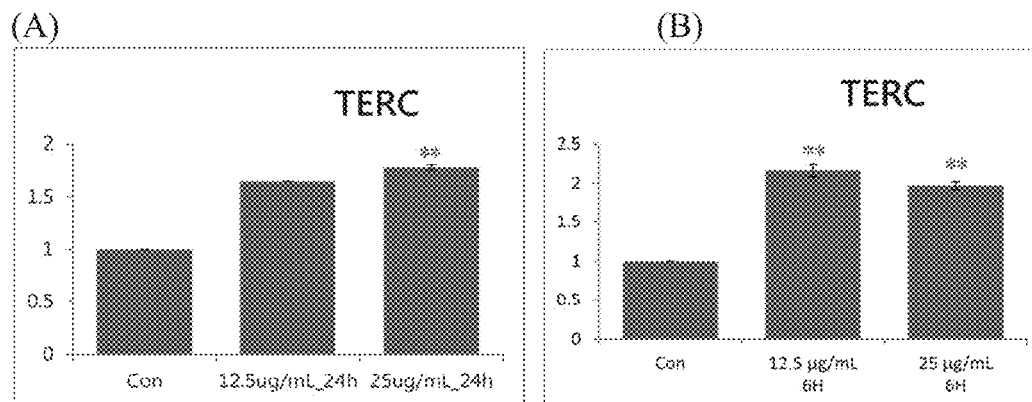
FIGS. 9 (A) and (B) show that in comparison with control (Con), Latrol-5 (A) and Latrol-6 (B) increase the expression of telomerase genes (TERC) in 24 hours and 6 hours, respectively.
Figure 10:
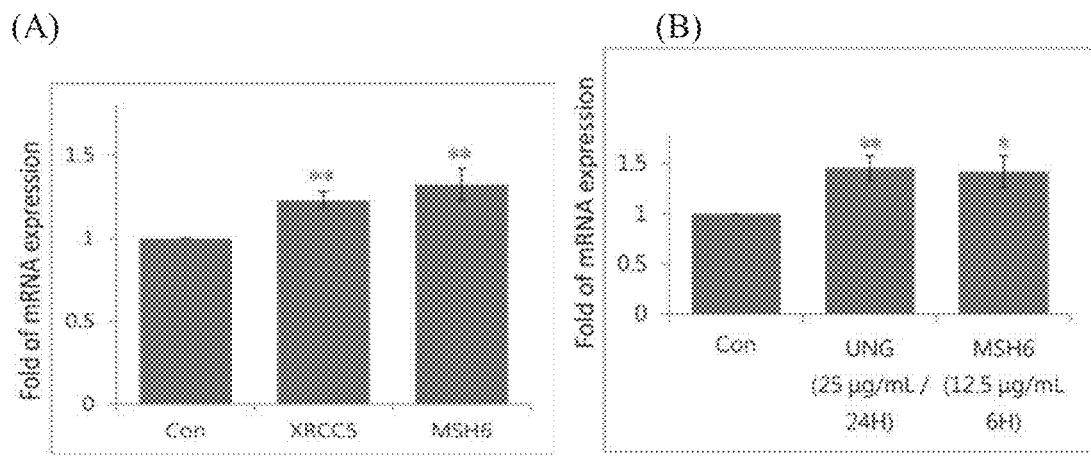
FIGS. 10 (A) and (B) show that in comparison with control (Con), Latrol-5 increases the expression of DNA repair genes (XRCC5 and/or MSH6) in 6 hours (A) and Latrol-6 increases the expression of DNA repair genes (UNG and MSH6) in 6 hours or 24 hours (B).
Figure 11:
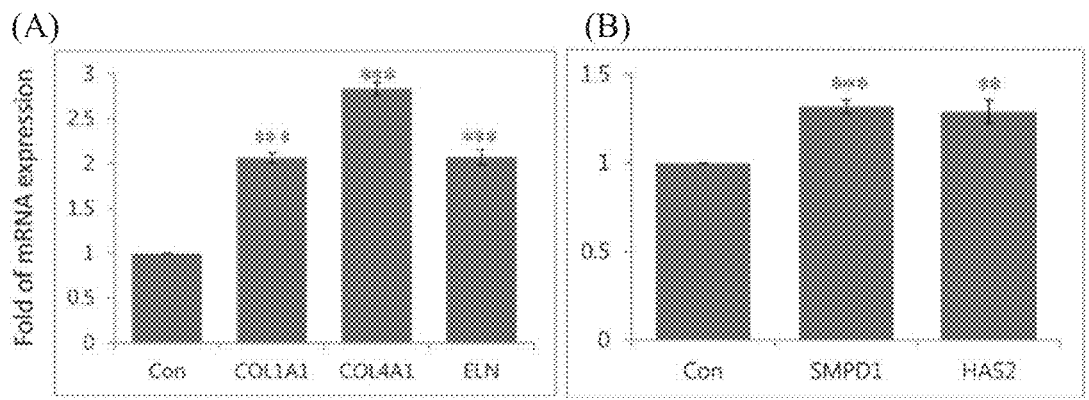
FIGS. 11 (A) and (B) show that in comparison with control (Con), Latrol-6 (25 μg/ml) increases the expression of collagen I gene (COL1A1), collagen IV gene (COL4A1) and elastin gene (ELN) in 24 hours (A), and the expression of SMPD1 (moisture-retention related gene) and/or HAS2 in 6 hours (B).
Figure 12:
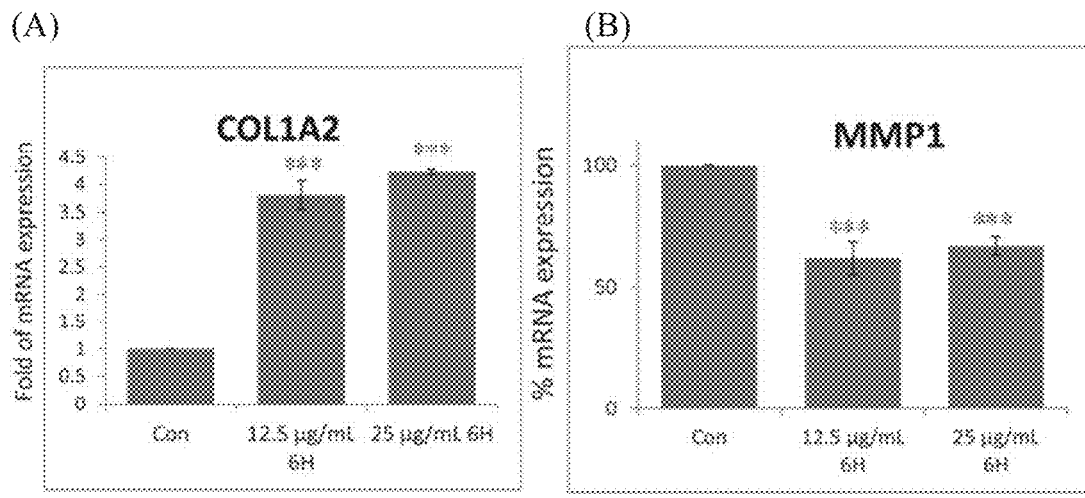
FIG. 12 (A) and (B) show that in comparison with control (Con), Latrol-5 (25 μg/ml) increases the expression of collagen I gene (COL1A2) in 6 hours, while inhibiting the expression of genes relating to collagen breakdown (MMP-1) in 6 hours (B).

The results show that Latrol-5 and Latrol-6 increase the expression of anti-aging genes (NADSYN, Atg1, MRPS5, CCT2 and/or CCT8) (FIG. 8 (A) and (B)), the expression of telomerase gene (TERC) (FIG. 9 (A) and (B)) and the expression of DNA repair genes (UNG, MSH6, XRCCS and/or MSH6) (FIG. 10 (A) and (B)). Moreover, Latrol-6 increases the expression of collagen I and IV genes, elastin genes, SMPD1 (moisture-retention related genes) and/or HSAS2 (FIG. 11 (A) and (B)). Latrol-6 increases the expression of collagen I gene, while inhibiting the expression of genes relating to collagen breakdown (MMP-1) (FIG. 12 (A) and (B)).

Figure 13:
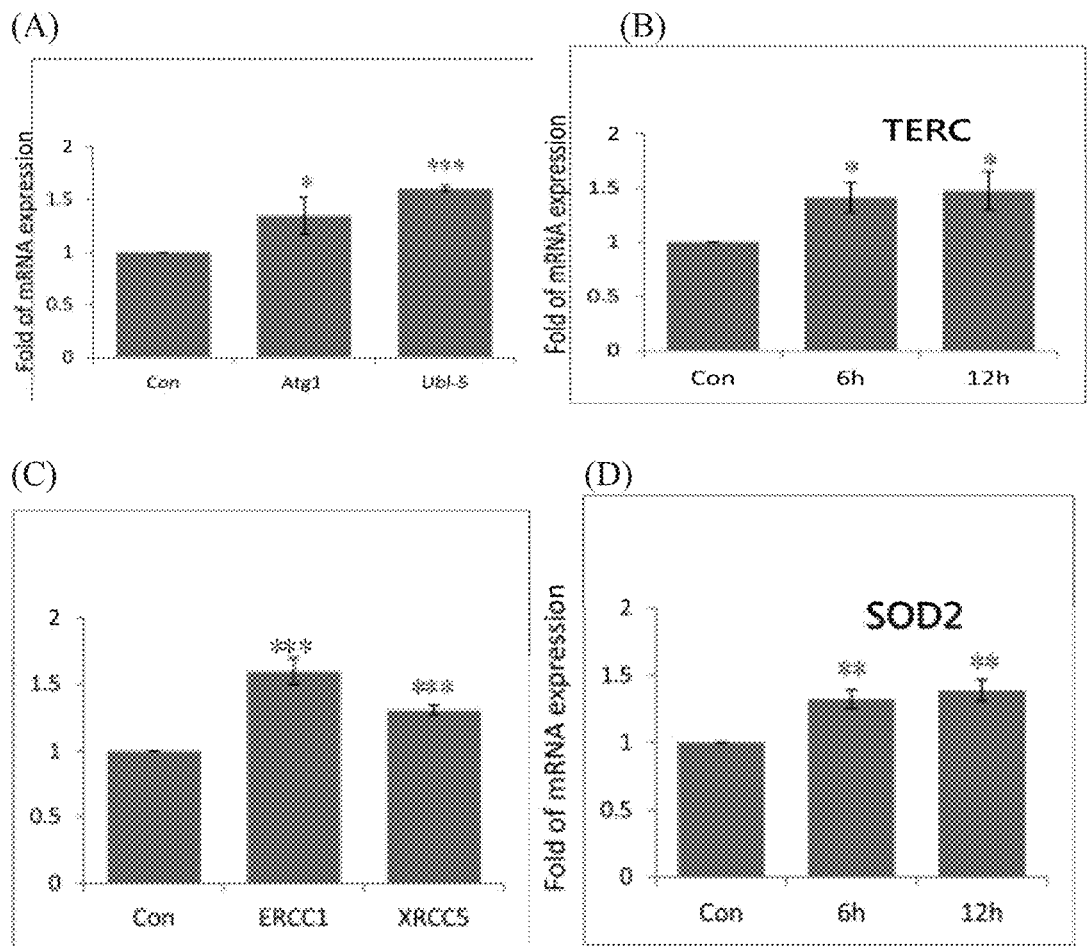
FIG. 13 (A) to (D) show that in comparison with control (Con), Heter-7 (25 μg/ml) increase the expression of anti-aging genes (Atg1 and Ub15) in 12 hours (A), the expression of telomerase gene (TERC) in 12 hours (B) and the expression of DNA repair genes (ERCC1 and XRCC5) (C) and the expression of anti-oxidation gene SOD2 (D).
Figure 14:
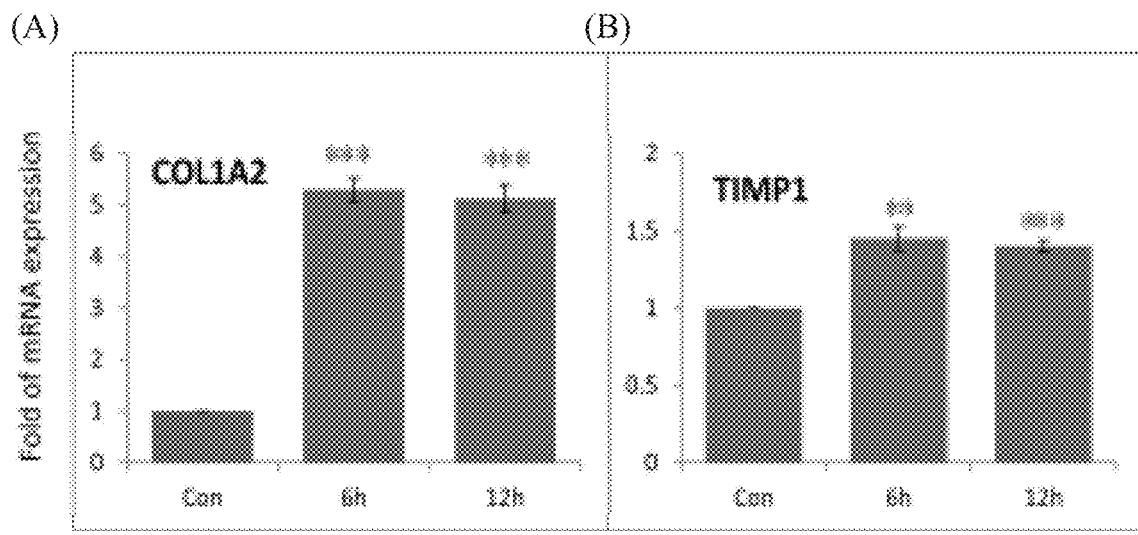
FIG. 14 (A) to (C) show that in comparison with control (Con), Heter-7 increases the expression of collagen I gene (12.5 μg/ml) (A) and TIMP1 gene (25 μg/ml) in 12 hours (B), while inhibiting MMP1 (2.5 μg/ml) in 12 hours (C).
Figure 14:
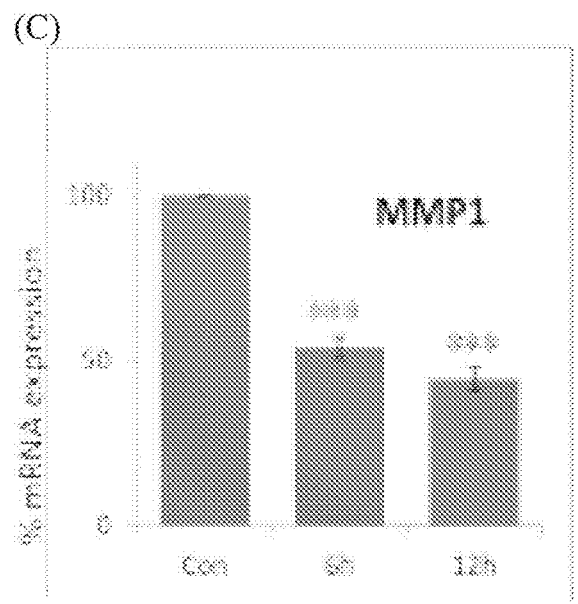

The results show that Heter-7 increases the expression of anti-aging genes (Atg1 and Ubl5) (FIG. 13 (A)), the expression of telomerase gene (TERC) (FIG. 13 (B)) and the expression of DNA repair genes (ERCC1 and XRCCS) (FIG. 13 (C)) and the expression of anti-oxidation gene SOD2 (FIG. 13 (D)). Moreover, Heter-7 increases the expression of collagen I gene (FIG. 14 (A)) and TIMP1 gene (FIG. 14 (B)), while inhibiting MMP1 (FIG. 14 (C)).

Figure 15:
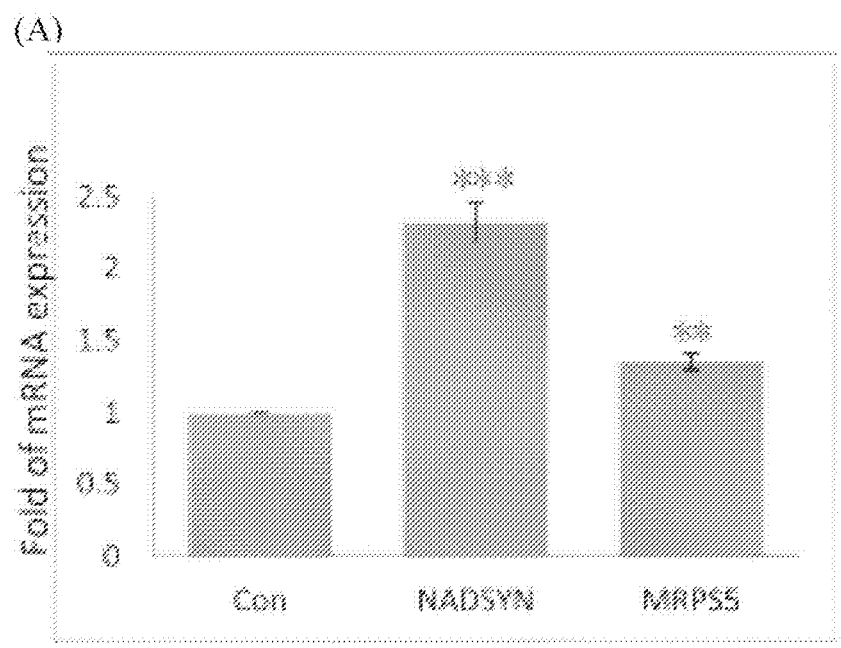
FIG. 15 (A) and (B) show that in comparison with control (Con), Chiro-8 (12.5 μg/ml) (A) and Chiro-5 (12.5 μg/ml) (B) increase the expression of anti-aging genes (NADSYN, 2c) MRPS5, Ub1-5 and/or FOXO) in 24 hours, respectively.
Figure 15:
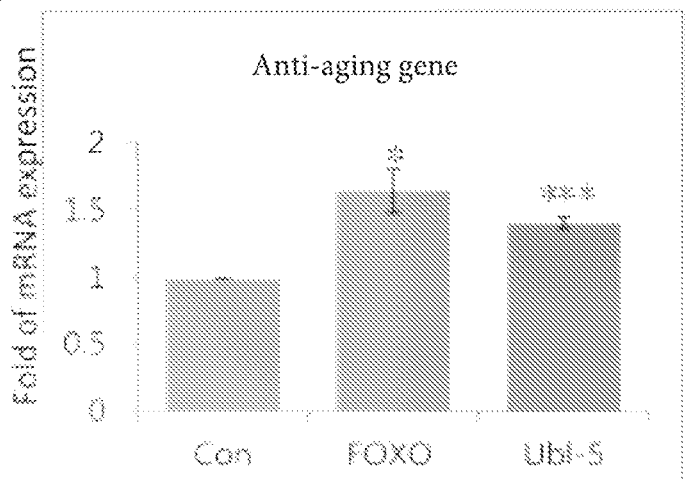
Figure 16:
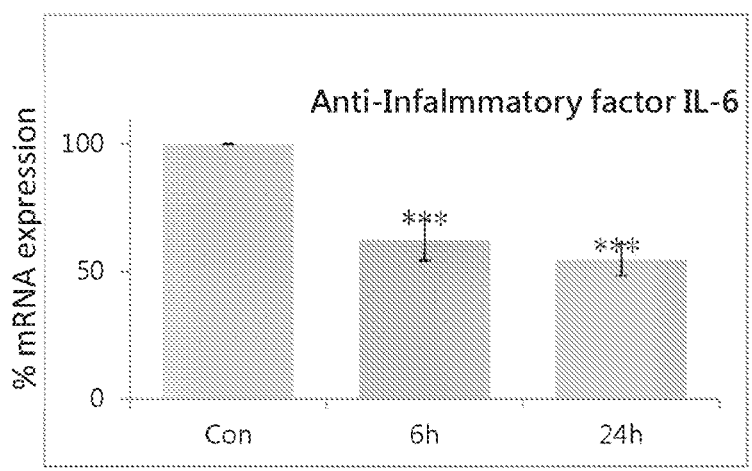
FIG. 16 shows that Chiro-8 inhibits the expression of anti-inflammatory factor IL-6 in 24 hours.
Figure 17:
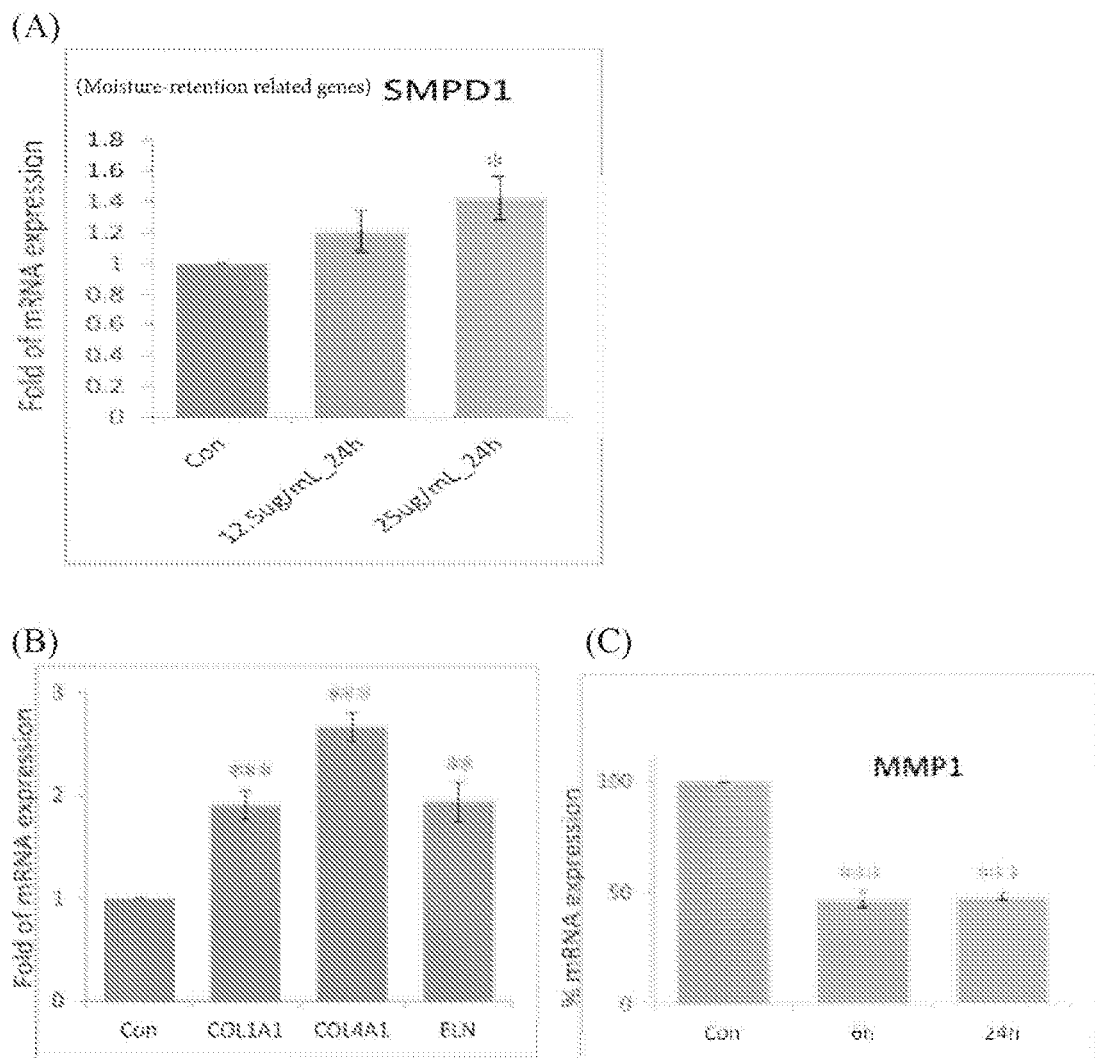
FIG. 17 (A) to (C) show that in comparison with control (Con), Chiro-8 (12.5 μg/ml and 25 μg/ml) increase the expression of moisture-retention related genes (SMPD1) in 24 hours (A) and Chiro-8 (12.5 μg/ml) increases the expression of collagen I gene (COLA1), collagen IV gene (COL4A1) and elastin gene (ELN) (B), while inhibiting the expression of MMP1 in 24 hours (C).
Figure 18:
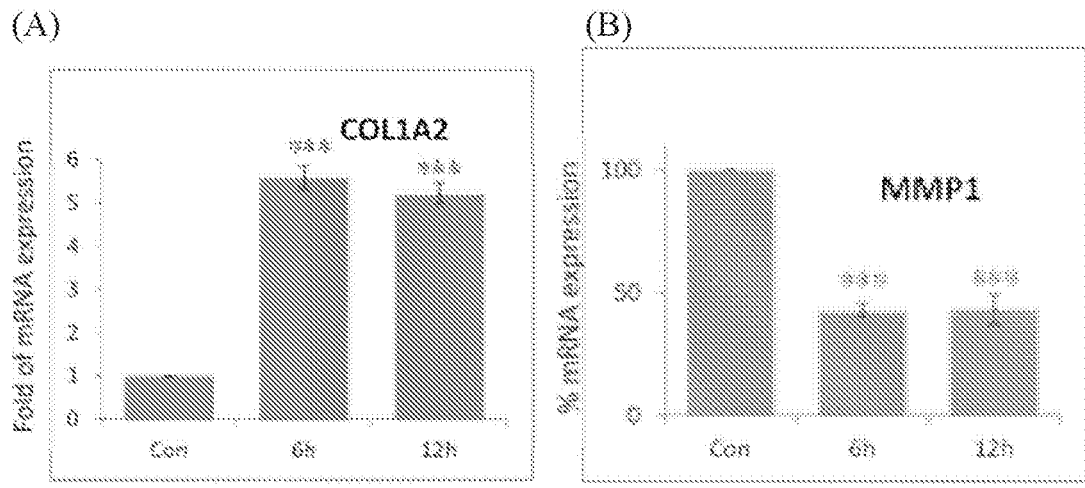
FIG. 18 (A) to (B) show that in comparison with control (Con), Chiro-5 (25 μg/ml) increase the expression of collagen I gene (COL1A2) (A), while inhibiting the expression of MMP1 (B).

The results show that Chiro-8 and Chiro-5 increase the expression of anti-aging genes (NADSYN, MRPS5, Ub1-5 and/or FOXO) (FIG. 15 (A) and (B)), and Chiro-8 inhibits the expression of anti-inflammatory factor IL-6 (FIG. 16). Moreover, Chiro-8 increases the expression of moisture-retention related genes (SMPD1) (FIG. 17 (A) and the expression of collagen I and elastin genes (FIG. 17 (B)), while inhibiting the expression of MMP1 (FIG. 17 (C)); and Chiro-5 increases the expression of collagen I gene (FIG. 18 (A)), while inhibiting the expression of MMP1 (FIG. 18 (B)).

What is claimed is:

1. A peptide derived from poison proteins from octopus or a salt thereof, consisting of a sequence of RPIK (SEQ ID NO: 7) or PRPIK (SEQ ID NO: 11).

2. The peptide of claim 1, wherein the octopus is *Hapalochlaena maculosa*.

3. A composition comprising the peptide or the salt of claim 1 and at least one carrier, diluent, or excipient.

4. The composition of claim 3, which is used in increasing production of elastin and/or hyaluronic acid in a subject.

5. The composition of claim 3, which is used in retarding aging in a subject.

6. The composition of claim 3, which is used in improving skin.

7. The composition of claim 3, which is used in inhibiting inflammation in a subject.

* * * * *

SEQUENCE LISTING

```
<160> NUMBER OF SEQ ID NOS: 16

<210> SEQ ID NO 1
<211> LENGTH: 4
<212> TYPE: PRT
<213> ORGANISM: Artificial Sequence
<220> FEATURE:
<223> OTHER INFORMATION: synthetic polypeptides
<220> FEATURE:
<221> NAME/KEY: X1
<222> LOCATION: (1)..(1)
<223> OTHER INFORMATION: X1 is selected from an amino acid having a
      positively charged side chain; X1 is K, R or H; X1 is K or R.
<220> FEATURE:
<221> NAME/KEY: X2
<222> LOCATION: (2)..(2)
<223> OTHER INFORMATION: X2 is selected from an amino acid having a
      uncharged side chain; X2 and X3 each independently is T, A I, C,
      S, G, Y, F, P or N; X2 and X3 each independently is T, C, S, G, Y,
      I, F, P, N or A.
<220> FEATURE:
<221> NAME/KEY: X3
<222> LOCATION: (3)..(3)
<223> OTHER INFORMATION: X3 is selected from an amino acid having an
      uncharged side chain; X2 and X3 each independently is T, A I, C,
      S, G, Y, F, P or N; X2 and X3 each independently is T, C, S, G, Y,
      I, F, P, N or A.
<220> FEATURE:
<221> NAME/KEY: X4
<222> LOCATION: (4)..(4)
<223> OTHER INFORMATION: X4 is selected from an amino acid having a
      positively charged side chain; X4 is K, R or H; X4 is K or R.

<400> SEQUENCE: 1

Xaa Xaa Xaa Xaa
1

<210> SEQ ID NO 2
<211> LENGTH: 4
<212> TYPE: PRT
<213> ORGANISM: Artificial Sequence
<220> FEATURE:
<223> OTHER INFORMATION: synthetic polypeptides

<400> SEQUENCE: 2

Arg Thr Cys Lys
1
```

```
<210> SEQ ID NO 3
<211> LENGTH: 4
<212> TYPE: PRT
<213> ORGANISM: Artificial Sequence
<220> FEATURE:
<223> OTHER INFORMATION: synthetic polypeptides

<400> SEQUENCE: 3

Lys Ser Gly Arg
1

<210> SEQ ID NO 4
<211> LENGTH: 4
<212> TYPE: PRT
<213> ORGANISM: Artificial Sequence
<220> FEATURE:
<223> OTHER INFORMATION: synthetic polypeptides

<400> SEQUENCE: 4

Lys Ser Gly Lys
1

<210> SEQ ID NO 5
<211> LENGTH: 4
<212> TYPE: PRT
<213> ORGANISM: Artificial Sequence
<220> FEATURE:
<223> OTHER INFORMATION: synthetic polypeptides

<400> SEQUENCE: 5

Lys Tyr Ile Lys
1

<210> SEQ ID NO 6
<211> LENGTH: 4
<212> TYPE: PRT
<213> ORGANISM: Artificial Sequence
<220> FEATURE:
<223> OTHER INFORMATION: synthetic polypeptides

<400> SEQUENCE: 6

Lys Ile Phe Lys
1

<210> SEQ ID NO 7
<211> LENGTH: 4
<212> TYPE: PRT
<213> ORGANISM: Artificial Sequence
<220> FEATURE:
<223> OTHER INFORMATION: synthetic polypeptides

<400> SEQUENCE: 7

Arg Pro Ile Lys
1

<210> SEQ ID NO 8
<211> LENGTH: 4
<212> TYPE: PRT
<213> ORGANISM: Artificial Sequence
<220> FEATURE:
<223> OTHER INFORMATION: synthetic polypeptides

<400> SEQUENCE: 8

Lys Asn Ala Lys
1

<210> SEQ ID NO 9
```

```
<211> LENGTH: 5
<212> TYPE: PRT
<213> ORGANISM: Artificial Sequence
<220> FEATURE:
<223> OTHER INFORMATION: synthetic polypeptides

<400> SEQUENCE: 9

Leu Lys Ser Gly Arg
1               5

<210> SEQ ID NO 10
<211> LENGTH: 5
<212> TYPE: PRT
<213> ORGANISM: Artificial Sequence
<220> FEATURE:
<223> OTHER INFORMATION: synthetic polypeptides

<400> SEQUENCE: 10

Lys Ile Phe Lys Phe
1               5

<210> SEQ ID NO 11
<211> LENGTH: 5
<212> TYPE: PRT
<213> ORGANISM: Artificial Sequence
<220> FEATURE:
<223> OTHER INFORMATION: synthetic polypeptides

<400> SEQUENCE: 11

Pro Arg Pro Ile Lys
1               5

<210> SEQ ID NO 12
<211> LENGTH: 6
<212> TYPE: PRT
<213> ORGANISM: Artificial Sequence
<220> FEATURE:
<223> OTHER INFORMATION: synthetic polypeptides

<400> SEQUENCE: 12

Thr Lys Ser Gly Lys Phe
1               5

<210> SEQ ID NO 13
<211> LENGTH: 6
<212> TYPE: PRT
<213> ORGANISM: Artificial Sequence
<220> FEATURE:
<223> OTHER INFORMATION: synthetic polypeptides

<400> SEQUENCE: 13

Val Lys Asn Ala Lys Tyr
1               5

<210> SEQ ID NO 14
<211> LENGTH: 7
<212> TYPE: PRT
<213> ORGANISM: Artificial Sequence
<220> FEATURE:
<223> OTHER INFORMATION: synthetic polypeptides

<400> SEQUENCE: 14

Gln Lys Arg Arg Thr Cys Lys
1               5

<210> SEQ ID NO 15
<211> LENGTH: 8
```

-continued

```
<212> TYPE: PRT
<213> ORGANISM: Artificial Sequence
<220> FEATURE:
<223> OTHER INFORMATION: synthetic polypeptides

<400> SEQUENCE: 15

Gln Arg Ile Lys Tyr Ile Lys Pro
1               5

<210> SEQ ID NO 16
<211> LENGTH: 7
<212> TYPE: PRT
<213> ORGANISM: Artificial Sequence
<220> FEATURE:
<223> OTHER INFORMATION: synthetic polypeptides

<400> SEQUENCE: 16

Pro Asp Ser Thr Glu Ala Lys
1               5
```